United States Patent
Yang et al.

(10) Patent No.: US 9,723,838 B2
(45) Date of Patent: Aug. 8, 2017

(54) PYRAZOLYL AMIDE COMPOUNDS AND USES THEREOF

(71) Applicant: SHENYANG SINOCHEM AGROCHEMICALS R&D CO., LTD., Liaoning (CN)

(72) Inventors: Huibin Yang, Liaoning (CN); Junwu Ying, Liaoning (CN); Yuquan Song, Liaoning (CN); Lin Chen, Liaoning (CN); Keke Li, Liaoning (CN); Xuegeng Shi, Liaoning (CN); Cong Feng, Liaoning (CN); Qi Huang, Liaoning (CN); Xiaoxi Fan, Liaoning (CN); Bin Li, Liaoning (CN)

(73) Assignee: Shenyang Sinochem Agrochemicals R&D Co., LTD, Liaoning (CN)

( * ) Notice: Subject to any disclaimer, the term of this patent is extended or adjusted under 35 U.S.C. 154(b) by 0 days.

(21) Appl. No.: 15/035,533

(22) PCT Filed: Nov. 24, 2014

(86) PCT No.: PCT/CN2014/092000
§ 371 (c)(1),
(2) Date: May 10, 2016

(87) PCT Pub. No.: WO2015/074615
PCT Pub. Date: May 28, 2015

(65) Prior Publication Data
US 2016/0286806 A1    Oct. 6, 2016

(30) Foreign Application Priority Data

Nov. 25, 2013  (CN) .......................... 2013 1 0606482
Nov. 25, 2013  (CN) .......................... 2013 1 0606491
Nov. 25, 2013  (CN) .......................... 2013 1 0606494

(51) Int. Cl.
*A01N 43/56*     (2006.01)
*C07D 401/04*    (2006.01)
*C07D 401/14*    (2006.01)

(52) U.S. Cl.
CPC ........... *A01N 43/56* (2013.01); *C07D 401/04* (2013.01); *C07D 401/14* (2013.01)

(58) Field of Classification Search
CPC .................................................. C07D 401/04
See application file for complete search history.

(56) References Cited

U.S. PATENT DOCUMENTS

| 7,541,377 | B2 | 6/2009 | Finkelstein et al. |
| 2004/0242645 | A1 | 12/2004 | Clark et al. |
| 2005/0261295 | A1 | 11/2005 | Stadtmueller et al. |
| 2010/0063293 | A1 | 3/2010 | Koyanagi et al. |

FOREIGN PATENT DOCUMENTS

| CN | 1543460 A | 11/2004 |
| CN | 1653051 A | 8/2005 |
| EP | 1598343 A1 | 11/2005 |
| EP | 2045253 A1 | 4/2009 |
| WO | 03/015519 A1 | 2/2003 |
| WO | 2008/072745 A1 | 6/2008 |
| WO | 2009/010260 A2 | 1/2009 |

OTHER PUBLICATIONS

International Search Report for PCT/CN2014/092000, dated Mar. 2, 2015 in English and Chinese Language.
International Preliminary Report on Patentability for International Application No. PCT/CN2014/092000 dated May 31, 2016, (Chinese with English translation) 16 pages.
Written Opinion of the International Searching Authority No. PCT/CN2014/092000 mailed Mar. 2, 2015, (Chinese with English translation) 14 pages.
Zhou, et al. Synthesis and SAR of Novel Di- and Trisubstituted 1,4-Dihydroquinoxaline-2, 3-diones Related to Licostinel (Acea 1021) as NMDA/Glycine Site Antagonists, Bioogranic & Medicinal Chemistry 11 (2003) 1769-1780.
Lahm, et al. Insecticidal anthranilic diamides: A new class of potent ryanodine receptor activators. Bioogranic & Medicinal Chemistry Letters 15, (2005), 4898-4906.
Moretto, el al. (αMe)Nva: stereoselective syntheses and preferred conformations of selected model peptides. J. Peptide Res., (2000), 56, 283-297.

(Continued)

*Primary Examiner* — Brian McDowell
(74) *Attorney, Agent, or Firm* — Smith, Gambrell & Russell, LLP

(57) ABSTRACT

Disclosed is a pyrazole amide compound of a novel structure as represented by general formula I, wherein, each substituent group is as defined in the specification. The compound of general formula I has good insecticidal activity, and can be used for pest control.

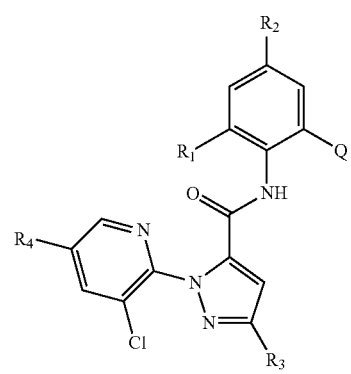

4 Claims, No Drawings

(56) References Cited

OTHER PUBLICATIONS

Garín, et al. On the Reaction of Anthranilic Acid with Thionyl Chloride: the Actual Structure of "Kamentani's Sulfinamide Anhydride". Tetrahedron Letters. vol. 32. No. 27, (1991), 3263-3264.

PYRAZOLYL AMIDE COMPOUNDS AND USES THEREOF

FIELD OF THE INVENTION

This invention belongs to the field of insecticide, relates to a kind of pyrazolyl amide compounds and uses thereof.

BACKGROUND OF THE INVENTION

The search for novel and improved insecticidal compounds or compositions are continually needed because of the resistance development of insect to the existing insecticides after a period of applications. Simultaneously, with the growing demands for agricultural and animal products, as well as the awareness on the environmental protection, the cost-effective or environmentally friendly novel insecticides are always needed.

The preparation and insecticidal activity of N-(1-amino-1-oxopropan-2-yl)benzamide compounds ($KC_1$, $KC_2$) were disclosed in CN1653051A, which have high activity against diamond back moth and armyworm.

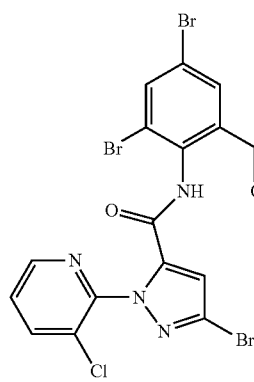

$KC_1$

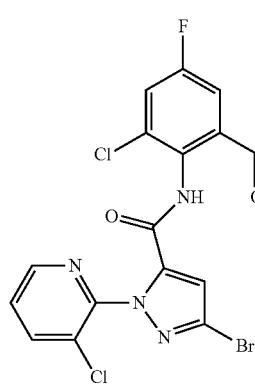

$KC_2$

Neither the preparation of pyrazolyl amide compounds, nor their insecticidal activities according to the present invention are described in state of the arts.

SUMMARY OF THE INVENTION

The purpose of this invention is to provide a kind of novel pyrazolyl amide compounds, and their applications for controlling insects in agriculture, forestry or public health.

The technical embodiments of this invention are as follows:

A kind of pyrazolyl amide compounds as represented by the general formula I:

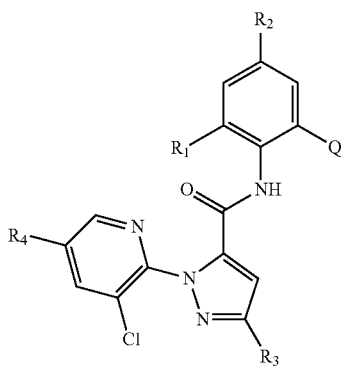

I

Wherein:
$R_1$ is F, Cl, Br or I;
$R_2$ is F, Cl, Br or I;
$R_3$ is Cl or Br;
$R_4$ is Cl or H;
Q is

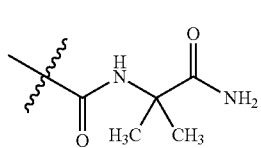

$Q_1$

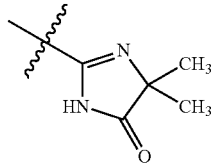

$Q_2$

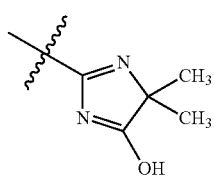

$Q_3$

The preferred compounds of the general formula I in this invention are:
$R_1$ is Cl or Br;
$R_2$ is Cl or Br;
$R_3$ is Cl or Br;
$R_4$ is Cl or H;
Q is $Q_1$, $Q_2$ or $Q_3$.

The more preferred compounds of the general formula I in this invention are:
$R_1$ is Cl;
$R_2$ is Cl;
$R_3$ is Cl or Br;
$R_4$ is H;
Q is $Q_1$ or $Q_2$ The technical embodiments of this invention also include the intermediates for preparing the general formula I which are not described in state of the arts according to the present invention, the compounds are as represented by the general formula II:

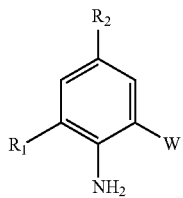

Wherein:
R₁ is F, Cl, Br or I;
R₂ is F, Cl, Br or I;
W is Q₁ or Q₃

The technical embodiments of this invention also include the preparation method of the general formula I, the reaction schemes are as follows:

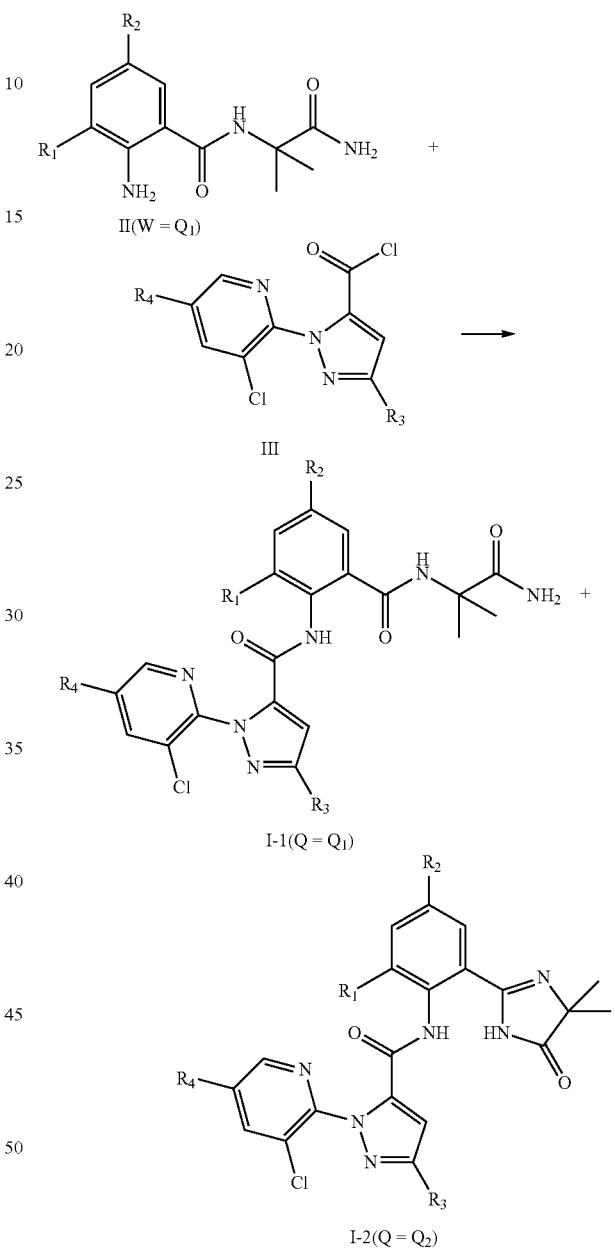

Wherein:
R₁ is F, Cl, Br or I;
R₂ is F, Cl, Br or I;
R₃ is Cl or Br;
R₄ is Cl or H;
Q is Q₁, Q₂ or Q₃.
W is Q₁ or Q₃

The compounds of general formula II and III are reacted in an appropriate solvent to yield the compounds of the general formula I at a certain temperature from −10° C. to boiling point for 30 minutes to 24 hours. The appropriate solvent is selected from hexane, benzene, toluene, acetonitrile, tetrahydrofuran, dichloromethane, dioxane, N, N-dimethylformamide or dimethyl sulfoxide etc.

The compounds of general formula I in the present invention can be prepared by the following method, and the substituents in the reaction schemes are as defined above:

When Q is Q₁ or Q₂, the compounds of the general formula I can be prepared by the following processes:

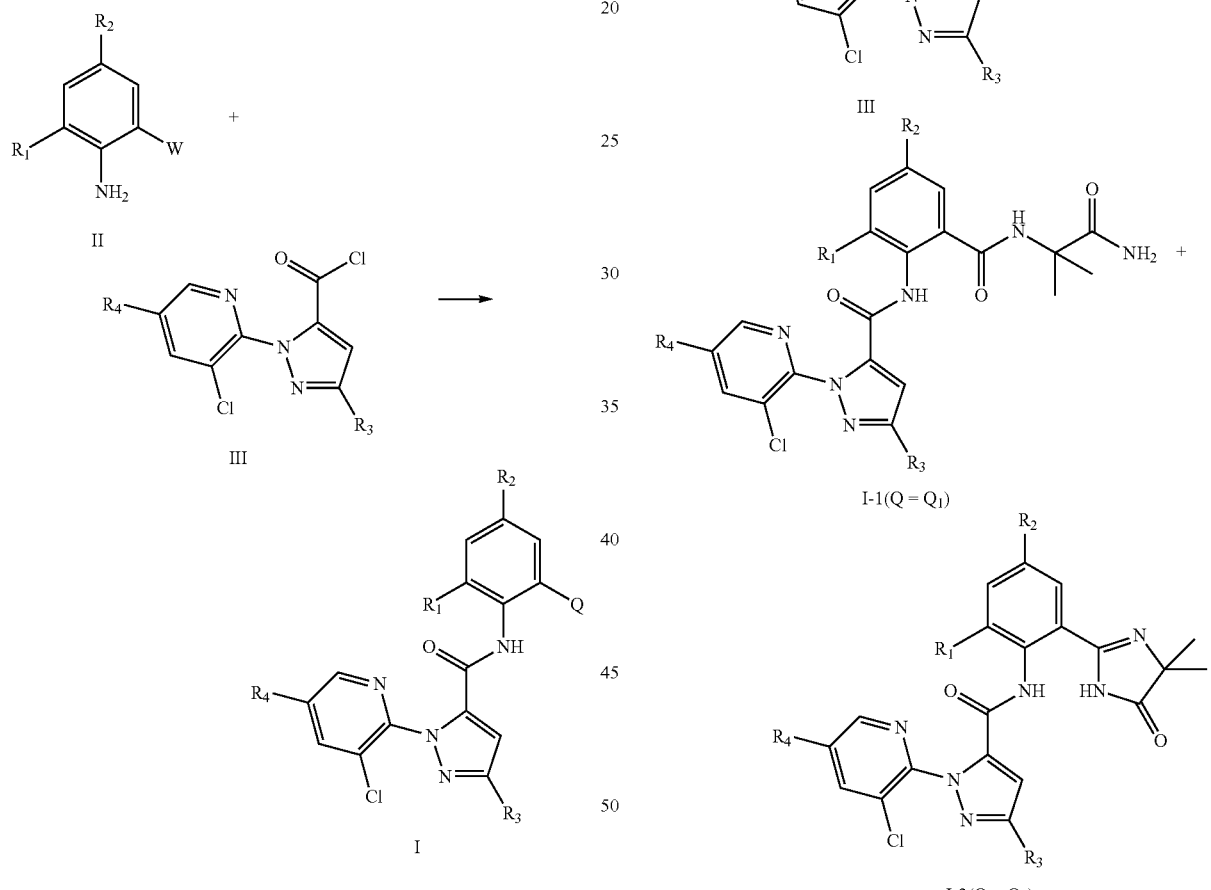

The compounds of general formula II (W=Q₁) and III are reacted in an appropriate solvent to yield the compounds of general formula I-1 (Q=Q₁) and I-2 (Q=Q₂) at a certain temperature from −10° C. to boiling point for 30 minutes to 24 hours. The appropriate solvent is selected from hexane, benzene, toluene, acetonitrile, tetrahydrofuran, dichloromethane, dioxane, N, N-dimethylformamide or dimethyl sulfoxide etc. When the temperature is between 0° C. and room temperature, the compounds of the general formula I-1 (Q=Q₁) are the main product. Relatively, the compounds of the general formula I-2 (Q=Q₂) can be mainly produced under reflux condition by using high boiling point solvent such as benzene, toluene, dioxane, N, N-dimethylformamide or dimethyl sulfoxide etc. The compounds of the general formula I-1 (Q=Q₁) and I-2 (Q=Q₂) can be separated by silica gel column chromatography or recrystallization etc.

When Q is Q₃, the compounds of the general formula I can be prepared by the following processes:

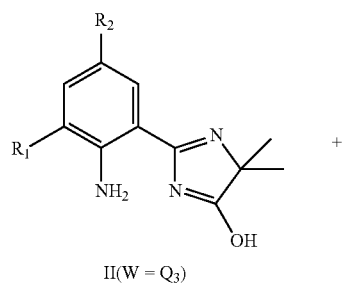

II(W = Q₃)

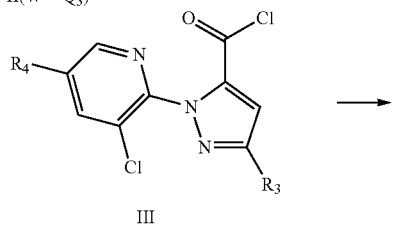

III

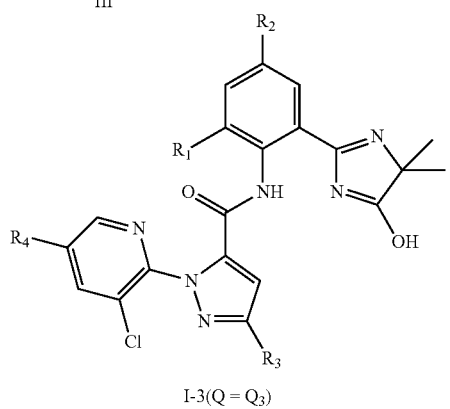

I-3(Q = Q₃)

The compounds of general formula II (W=Q₃) and III are reacted in an appropriate solvent to yield the compounds of the general formula I-3 (Q=Q₃) at a certain temperature from −10° C. to boiling point for 30 minutes to 24 hours. The appropriate solvent is selected from hexane, benzene, toluene, acetonitrile, tetrahydrofuran, N, N-dimethylformamide or dimethyl sulfoxide etc.

The procedures of general formula III (the pyrazole formyl chloride and its corresponding carboxylic acid) can be prepared according to the procedures as described in the following references: *Bioorganic & Medicinal Chemistry Letters*, 2005, 15, 4898-4906; WO03/015519A1; WO2008/072745A1 and WO 2009/010260A2.

The compounds of the general formula II can be prepared by the following processes:

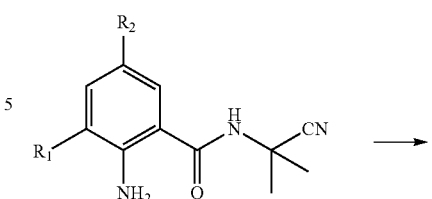

IV

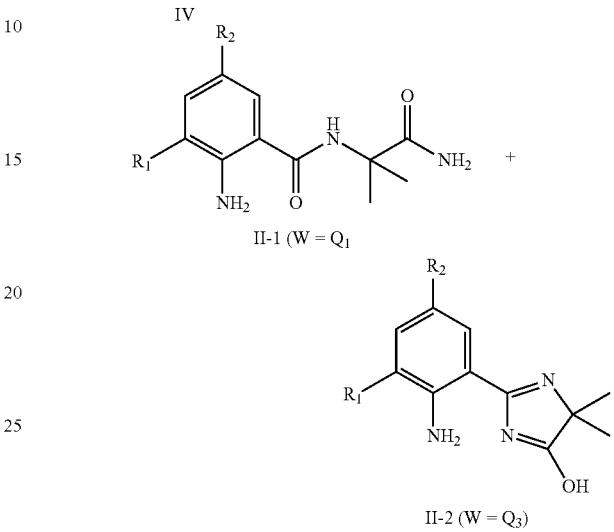

II-1 (W = Q₁)

II-2 (W = Q₃)

The compounds of general formula IV reacted with hydrogen peroxide in an appropriate solvent to yield the compounds of general formula II at a certain temperature from −10° C. to boiling point for 30 minutes to 48 hours under alkaline condition. The appropriate solvent is selected from hexane, benzene, toluene, ethyl acetate, ethanol, acetonitrile, tetrahydrofuran, dioxane, N, N-dimethylformamide or dimethyl sulfoxide etc. The appropriate base is selected from sodium hydroxide or potassium hydroxide etc. When the temperature is 0° C.-room temperature the compounds of the general formula II-1 (W=Q₁) are mainly produced. Relatively, the compounds of the general formula II-2 (W=Q₃) can be mainly produced when the temperature is 70° C.-110° C. The compounds of the general formula II-1 (W=Q₁) and II-2 (W=Q₃) can be separated by silica gel column chromatography or recrystallization etc.

The general formula II-2 (W=Q₃) can be prepared from the general formula II-1 (W=Q₁) by the following processes:

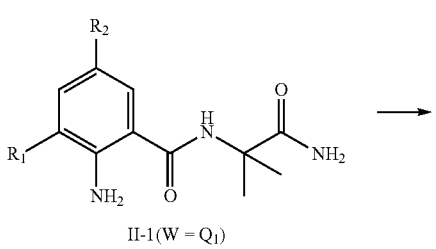

II-1(W = Q₁)

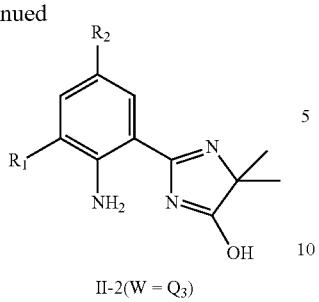

II-2(W = Q₃)

The compounds of the general formula II-1 (W=Q₁) are reacted in an appropriate solvent to yield the compounds of general formula II-2 (W=Q₃) at a certain temperature from −10° C. to boiling point for 30 minutes to 48 hours under alkaline conditions. The appropriate solvent is selected from hexane, benzene, toluene, ethyl acetate, ethanol, acetonitrile, tetrahydrofuran, dioxane, N, N-dimethylformamide or dimethyl sulfoxide etc.

The appropriate base is selected from organic base such as triethylamine, N, N-dimethyl aniline, pyridine, tert-butyl alcohol sodium and tert-butyl alcohol potassium etc., or inorganic base such as sodium hydroxide, potassium hydroxide and sodium methoxide etc.

The compounds of the general formula IV can be prepared by the following processes:

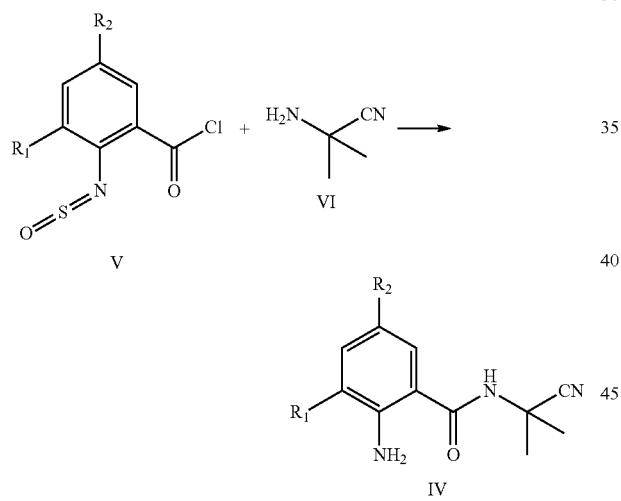

The compounds of the general formula V and the compounds of the general formula VI (commercial available or prepared by the following references: *J. Peptide Res.* 56, 2000, 283-297) are reacted in an appropriate solvent to yield the compounds of general formula IV at a certain temperature from −10° C. to boiling point for 30 minutes to 48 hours under alkaline conditions. The appropriate solvent is selected from chloroform, dichloromethane, carbon tetrachloride, hexane, benzene, toluene, ethyl acetate, N, N-dimethylformamide, tetrahydrofuran or dioxane etc. The appropriate base is advantageous to the reaction which is selected from triethylamine, pyridine, sodium hydroxide, potassium hydroxide, sodium carbonate, potassium carbonate or sodium hydrogen carbonate etc.

The compounds of general formula V can be prepared according to the procedures as described in the following references: *Bioorganic & Medicinal Chemistry*, (2003), 11, 1769-1780; *Bioorganic & Medicinal Chemistry Letters*, 2005, 15, 4898-4906 and *Tetrahedron Letters*, 1991, 32, 3263-3264.

The table 1 shows the structures and their physical properties of some representative compounds of general formula I:

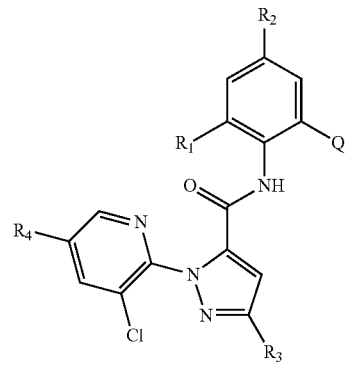

TABLE 1

| Compound | R₁ | R₂ | R₃ | R₄ | Q | Appearance | M.p. |
|---|---|---|---|---|---|---|---|
| 1.1 | F | Cl | Cl | H | Q₁ | | |
| 1.2 | F | Cl | Br | H | Q₁ | | |
| 1.3 | Cl | Cl | Cl | H | Q₁ | white solid | 158-162° C. |
| 1.4 | Cl | Cl | Br | H | Q₁ | white solid | 164-168° C. |
| 1.5 | Br | Cl | Cl | H | Q₁ | white solid | 163-167° C. |
| 1.6 | Br | Cl | Br | H | Q₁ | white solid | 167-171° C. |
| 1.7 | Cl | F | Cl | H | Q₁ | white solid | 166-171° C. |
| 1.8 | Cl | F | Br | H | Q₁ | white solid | 169-174° C. |
| 1.9 | Br | Br | Cl | H | Q₁ | white solid | 165-169° C. |
| 1.10 | Br | Br | Br | H | Q₁ | white solid | 172-175° C. |
| 1.11 | Br | F | Cl | H | Q₁ | | |
| 1.12 | Br | F | Br | H | Q₁ | | |
| 1.13 | Cl | Cl | Br | Cl | Q₁ | white solid | 169-173° C. |
| 1.14 | Br | Br | Cl | Cl | Q₁ | | |
| 1.15 | Br | Br | Br | Cl | Q₁ | | |
| 1.16 | Br | Cl | Cl | Cl | Q₁ | | |
| 1.17 | Br | Cl | Br | Cl | Q₁ | | |
| 1.18 | F | Cl | Cl | H | Q₂ | | |
| 1.19 | F | Cl | Br | H | Q₂ | | |
| 1.20 | Cl | Cl | Cl | H | Q₂ | white solid | 152-157° C. |
| 1.21 | Cl | Cl | Br | H | Q₂ | white solid | 162-164° C. |
| 1.22 | Br | Cl | Cl | H | Q₂ | yellow solid | 158-162° C. |
| 1.23 | Br | Cl | Br | H | Q₂ | yellow solid | 160-165° C. |
| 1.24 | Cl | F | Cl | H | Q₂ | yellow solid | 241-245° C. |
| 1.25 | Cl | F | Br | H | Q₂ | yellow solid | 261-265° C. |
| 1.26 | Br | Br | Cl | H | Q₂ | white solid | 167-171° C. |
| 1.27 | Br | Br | Br | H | Q₂ | yellow solid | 164-168° C. |
| 1.28 | Cl | Cl | Br | Cl | Q₂ | white solid | 162-165° C. |
| 1.29 | Br | Br | Cl | Cl | Q₂ | | |
| 1.30 | Br | Br | Br | Cl | Q₂ | | |
| 1.31 | Br | Cl | Cl | Cl | Q₂ | | |
| 1.32 | Br | Cl | Br | Cl | Q₂ | | |
| 1.33 | F | Cl | Cl | H | Q₃ | | |
| 1.34 | F | Cl | Br | H | Q₃ | | |
| 1.35 | Cl | Cl | Cl | H | Q₃ | white solid | 192-194° C. |
| 1.36 | Cl | Cl | Br | H | Q₃ | white solid | 182-184° C. |
| 1.37 | Br | Br | Cl | H | Q₃ | white solid | 181-182° C. |
| 1.38 | Br | Br | Br | H | Q₃ | white solid | 182-184° C. |
| 1.39 | Cl | Cl | Br | Cl | Q₃ | white solid | 184-187° C. |
| 1.40 | Cl | Cl | Cl | Cl | Q₃ | white solid | 201-202° C. |

¹H NMR (300 MHz, DMSO-d₆) data of representative compounds:

Compound 1.3: 10.44 (s, 1H), 8.44 (dd, 1H), 8.23 (s, 1H), 8.05 (dd, 1H), 7.69 (d, 1H), 7.65 (d, 1H), 7.55 (dd, 1H), 7.33 (s, 1H), 7.03 (s, 1H), 6.67 (s, 1H), 1.30 (s, 6H).

Compound 1.4: 10.34 (d, 1H), 8.45 (d, 1H), 7.84 (dd, 1H), 7.33 (dd, 1H), 7.23 (s, 1H), 7.18 (d, 1H), 7.12 (d, 1H), 6.89 (s, 1H), 6.33 (s, 1H), 5.58 (s, 1H), 1.55 (s, 6H).

Compound 1.5: 10.45 (s, 1H), 8.44 (d, 1H), 8.20 (s, 1H), 8.06 (d, 1H), 7.80 (d, 1H), 7.73 (d, 1H), 7.56 (dd, 1H), 7.33 (s, 1H), 7.03 (s, 1H), 6.67 (s, 1H), 1.29 (s, 6H).

Compound 1.6: 10.44 (s, 1H), 8.45 (dd, 1H), 8.22 (s, 1H), 8.09 (d, 1H), 7.83 (d, 1H), 7.76 (d, 1H), 7.56 (dd, 1H), 7.40 (s, 1H), 7.05 (s, 1H), 6.70 (s, 1H), 1.28 (s, 6H).

Compound 1.7: 10.38 (s, 1H), 8.44 (dd, 1H), 8.13 (s, 1H), 8.05 (d, 1H), 7.55 (dd, 1H), 7.49 (s, 1H), 7.46 (s, 1H), 7.33 (s, 1H), 7.00 (s, 1H), 6.67 (s, 1H), 1.33 (s, 6H).

Compound 1.8: 10.37 (s, 1H), 8.44 (d, 1H), 8.14 (s, 1H), 8.06 (d, 1H), 7.56 (dd, 1H), 7.51 (s, 1H), 7.48 (s, 1H), 7.39 (s, 1H), 7.01 (s, 1H), 6.68 (s, 1H), 1.25 (s, 6H).

Compound 1.9: 10.42 (s, 1H), 8.43 (d, 1H), 8.16 (s, 1H), 8.03 (d, 1H), 7.89 (d, 1H), 7.82 (d, 1H), 7.54 (dd, 1H), 7.34 (s, 1H), 6.98 (s, 1H), 6.60 (s, 1H), 1.26 (s, 6H).

Compound 1.10: 10.48 (s, 1H), 8.84 (s, 1H), 8.43 (dd, 1H), 8.03 (dd, 1H), 7.94 (d, 1H), 7.61 (d, 1H), 7.54 (dd, 1H), 7.34 (s, 1H), 6.98 (s, 1H), 6.60 (s, 1H), 1.26 (s, 6H).

Compound 1.13: 10.53 (s, 1H), 8.59 (d, 1H), 8.51 (d, 1H), 8.36 (s, 1H), 7.82 (dd, 1H), 7.43 (s, 1H), 7.17 (s, 1H), 6.83 (s, 1H), 1.26 (s, 6H).

Compound 1.20: 10.52 (s, 1H), 8.90 (s, 1H), 8.44 (dd, 1H), 8.09 (dd, 1H), 7.79 (d, 1H), 7.57 (dd, 1H), 7.50 (d, 1H), 7.38 (s, 1H), 1.58 (s, 6H).

Compound 1.21: 10.50 (s, 1H), 8.88 (s, 1H), 8.43 (d, 1H), 8.06 (d, 1H), 7.73 (d, 1H), 7.55 (dd, 1H), 7.48 (d, 1H), 7.44 (s, 1H), 1.51 (s, 6H).

Compound 1.22: 10.52 (s, 1H), 8.88 (d, 1H), 8.44 (d, 1H), 8.08 (d, 1H), 7.90 (d, 1H), 7.56 (dd, 1H), 7.52 (d, 1H), 7.39 (s, 1H), 1.51 (s, 6H).

Compound 1.23: 9.42 (s, 1H), 8.41 (dd, 1H), 7.83 (dd, 1H), 7.38 (dd, 1H), 7.35 (s, 1H), 7.29 (d, 1H), 7.20 (d, 1H), 7.05 (s, 1H), 1.51 (s, 6H).

Compound 1.24: 10.44 (s, 1H), 8.83 (s, 1H), 8.45 (d, 1H), 8.09 (d, 1H), 7.62 (dd, 1H), 7.57 (dd, 111), 7.37 (s, 1H), 7.32 (dd, 1H), 1.52 (s, 6H).

Compound 1.25: 10.45 (s, 1H), 8.86 (s, 1H), 8.46 (dd, 1H), 8.12 (dd, 1H), 7.70 (dd, 1H), 7.59 (dd, 1H), 7.44 (s, 1H), 7.37 (dd, 1H), 1.52 (s, 6H).

Compound 1.26: 10.48 (s, 1H), 8.83 (s, 1H), 8.43 (d, 1H), 8.03 (d, 1H), 7.95 (d, 1H), 7.61 (d, 1H), 7.54 (dd, 1H), 7.37 (s, 1H), 1.52 (s, 6H).

Compound 1.27: 10.48 (s, 1H), 8.84 (s, 1H), 8.43 (dd, 1H), 8.03 (dd, 1H), 7.94 (d, 1H), 7.61 (d, 1H), 7.54 (dd, 1H), 7.44 (s, 1H), 1.52 (s, 6H).

Compound 1.28: 10.62 (s, 1H), 8.96 (s, 1H), 8.61 (d, 1H), 8.53 (d, 1H), 7.90 (d, 1H), 7.57 (d, 1H), 7.48 (s, 1H), 1.52 (s, 6H).

Compound 1.35: 11.16 (s, 1H), 10.64 (s, 1H), 8.45 (dd, 1H), 8.12 (dd, 1H), 7.89 (s, 1H), 7.68 (d, 1H), 7.58 (dd, 1H), 7.34 (s, 1H), 1.13 (s, 6H).

Compound 1.36: 11.17 (s, 1H), 10.62 (s, 1H), 8.48 (dd, 1H), 8.15 (d, 1H), 7.95 (s, 1H), 7.70 (d, 1H), 7.56 (dd, 1H), 7.42 (s, 1H), 1.15 (s, 6H).

Compound 1.37: 10.62-11.19 (m, 2H), 8.42 (dd, 1H), 8.03 (d, 1H), 7.99 (s, 1H), 7.83 (d, 1H), 7.54 (dd, 1H), 7.25 (s, 1H), 1.15 (s, 6H).

Compound 1.38: 10.52-11.27 (m, 2H), 8.47 (d, 1H), 8.17 (s, 1H), 8.14 (s, 1H), 7.85 (s, 1H), 7.61 (dd, 1H), 7.42 (s, 1H), 1.12 (s, 6H).

Compound 1.39: 11.48 (s, 1H), 10.98 (s, 1H), 8.37 (s, 1H), 7.83 (s, 1H), 7.51 (s, 1H), 7.45 (s, 1H), 6.99 (s, 1H), 1.38 (s, 6H).

Compound 1.40: 10.35-11.45 (m, 2H), 8.58 (d, 1H), 8.51 (d, 1H), 7.95 (d, 1H), 7.72 (d, 1H), 7.37 (s, 1H), 1.12 (s, 6H).

The table 2 shows the structures and their physical properties of some representative compounds of general formula II:

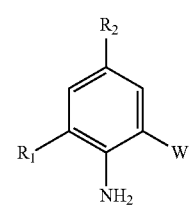

II

TABLE 2

| Compound | $R_1$ | $R_2$ | W | Appearance | M.p. |
|---|---|---|---|---|---|
| 2.1 | Cl | Cl | $Q_1$ | white solid | 166-168° C. |
| 2.2 | Cl | F | $Q_1$ | white solid | 169-171° C. |
| 2.3 | Cl | Br | $Q_1$ | | |
| 2.4 | Br | Br | $Q_1$ | white solid | 178-182° C. |
| 2.5 | Br | Cl | $Q_1$ | | |
| 2.6 | Br | F | $Q_1$ | | |
| 2.7 | F | F | $Q_1$ | | |
| 2.8 | F | Br | $Q_1$ | | |
| 2.9 | F | Cl | $Q_1$ | | |
| 2.10 | Cl | Cl | $Q_3$ | white solid | 170-173° C. |
| 2.11 | Cl | F | $Q_3$ | white solid | 180-184° C. |
| 2.12 | Br | Br | $Q_3$ | white solid | 180-183° C. |
| 2.13 | Cl | Br | $Q_3$ | | |
| 2.14 | Br | F | $Q_3$ | | |
| 2.15 | F | F | $Q_3$ | | |
| 2.16 | F | Cl | $Q_3$ | | |
| 2.17 | F | Br | $Q_3$ | | |

$^1$H NMR (300 MHz, DMSO-$d_6$) data of representative compounds:

Compound 2.1: 7.35 (d, 1H), 7.27 (d, 1H), 6.80 (s, 1H), 6.15 (br, s, 1H), 5.99 (s, 2H), 5.55 (br, s, 1H), 1.69 (s, 6H).

Compound 2.2: 7.17 (d, 1H), 7.06 (d, 1H), 6.82 (s, 1H), 6.15 (br, s, 1H), 5.75 (br, s, 2H), 5.55 (br, s, 1H), 1.70 (s, 6H).

Compound 2.4: 8.23 (s, 1H), 7.79 (d, 1H), 7.59 (d, 1H), 7.05 (s, 1H), 6.65 (s, 1H), 6.35 (s, 2H), 1.37 (s, 6H).

Compound 2.10: 10.75 (s, 1H), 7.46 (d, 1H), 7.38 (d, 1H), 6.94 (s, 2H), 1.48 (s, 6H).

Compound 2.11: 10.76 (s, 1H), 7.26 (d, 1H), 7.23 (d, 1H), 6.76 (s, 2H), 1.45 (s, 6H).

Compound 2.12: 10.65 (s, 1H), 7.65 (d, 1H), 7.61 (d, 1H), 7.03 (s, 2H), 1.47 (s, 6H).

The liposolubility of the organic molecule can be improved by changing hydrogen to methyl, which is closely related to the mobility of the molecule in the biological organisms such as insects, or plants. The suitable transportation properties of bioactive molecules play an important role in the biological efficacy. The transportation suitability of molecules is unpredictable, so it only can be discovered through extensively creative investigation.

The pyrazolyl amide compounds of the general formula I in this invention possess surprisingly high insecticidal activity compared with the known N-(1-amino-1-oxopropan-2-yl)benzamide compounds. So, this invention also provides the use of the general formula I compounds for pest control.

Another embodiment of this invention includes the insecticidal compositions, in which the compounds of general formula I are active ingredients. The weight percentage of active ingredient(s) in the compositions is from 1% to 99%. There are also acceptable carriers in agriculture, forestry or public health in these compositions. Active ingredients according to general formula I compounds, can be a single compound, or can be a mixture of two or more compounds of general formula I. For example, active ingredients can contain one, two or three compounds of general formula I-1 (Q=Q₁), I-2 (Q=Q₂) and I-3 (Q=Q₃).

The compositions of the present invention can be used in the form of various formulations. Usually, the compounds of general formula I as the active ingredient can be dissolved in or dispersed to carriers or made to a formulation. So that they can be easily dispersed as an insecticide, such as a wettable powder or an emulsifiable concentrate etc. Therefore, in these compositions, at least a liquid or solid carrier is added, and usually suitable surfactant(s) can be added when needed.

Also provided by this invention are the application methods for pest control, which is to apply the compositions of the present invention to the growing loci of the insects as mentioned above. The suitably effective dosage of the compounds of the present invention is usually within a range of 10 g/ha to 1000 g/ha.

For some applications, one or more other fungicides, insecticides, herbicides, plant growth regulators or fertilizer can be added into the insecticidal compositions of the present invention to make additional merits and effects.

It shall be noted that variations and changes are permitted within the claimed scopes in the present invention.

DESCRIPTION OF THE INVENTION IN DETAIL

The following synthesis examples and results of biological tests are used to further illustrate the present invention, but not to limit it.

SYNTHESIS EXAMPLES

Example 1: Synthesis of Compound 1.4 and 1.21

(1) Synthesis of 2-amino-2-methylpropanenitrile

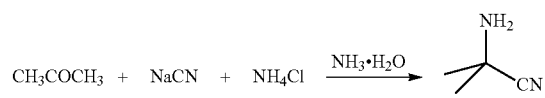

A solution of sodium cyanide (4.95 g, 100 mmol) and aqueous ammonia (60 mL) was stirred at room temperature till the sodium cyanide was completely dissolved, acetone (5.84 g, 100 mmol) and ammonium chloride (5.38 g, 100 mmol) were added. The reaction mixture was stirred for 48 hours at room temperature. The mixture was extracted with dichloromethane (3×50 mL). The organic layer was dried over anhydrous magnesium sulfate and concentrated to give the product (5.25 g) as a colorless oil in 57% yield.

¹H NMR (300 MHz, CDCl₃): 1.84 (br, s, 2H), 1.50 (s, 6H).

(2) Synthesis of 2-amino-3,5-dichlorobenzoic acid

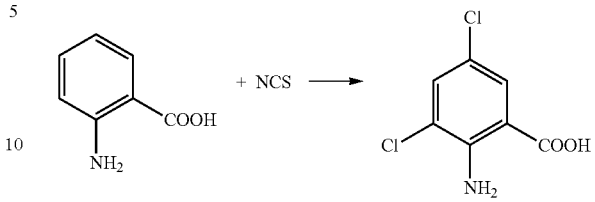

A slurry of 2-aminobenzoic acid (50 g, 365 mmol) and N,N-dimethylformamide (400 mL) was stirred in a flask with three necks at room temperature till the 2-aminobenzoic acid was completely dissolved, 1-chloropyrrolidine-2,5-dione (102.4 g, 767 mmol) was added. The reaction mixture was stirred for 1 hour at 80° C. The mixture was poured into ice water with stirring vigorously. The solid that precipitated was collected by filtration, rinsed with water 2 times and air dried to give the product (68 g) as a yellow solid in 90.4% yield. Melting point: 201-204° C.

(3) Synthesis of 2-amino-3,5-dichloro-N-(2-cyanopropan-2-yl)benzamide

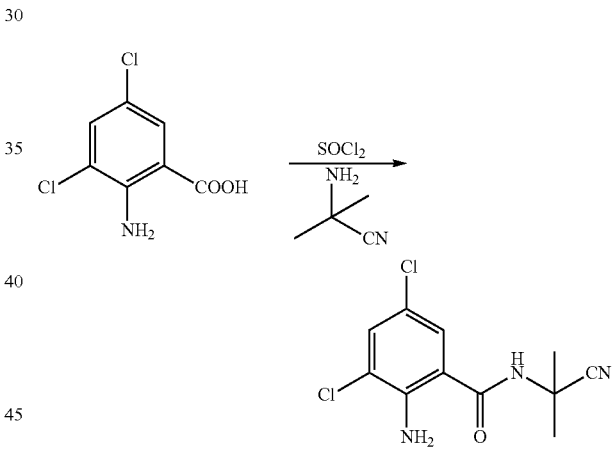

A solution of 2-amino-3,5-dichlorobenzoic acid (10 g, 48.5 mmol) and sulfurous dichloride (23.1 g, 194 mmol) was heated to reflux for 3 hours. The reaction mixture was evaporated to dryness at reduced pressure to give a red oil.

A solution of 2-amino-2-methylpropanenitrile (4.08 g, 48.5 mmol) and triethylamine (7.36 g, 72.7 mmol) in tetrahydrofuran (200 mL) was slowly added the red oil above in tetrahydrofuran (50 mL) at room temperature. The mixture was stirred for 12 hours at room temperature and then concentrated to dryness under vacuum. The resulting residue was extracted with ethyl acetate (500 mL) and water (100 mL). The organic layer was washed with saturated brine (50 mL), dried over anhydrous magnesium sulfate and concentrated to give a solid, which is triturated with a mixture of 25% ethyl acetate/petroleum ether to give a yellow solid (8.7 g) in 66% yield.

(4) Synthesis of Compound 2.1 and 2.10

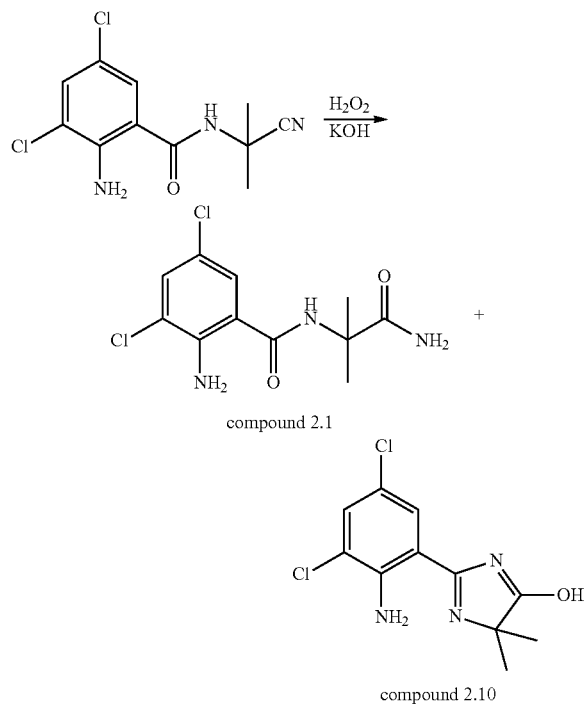

compound 2.1 compound 2.10

(5) Synthesis of Compound 1.4 and 1.21

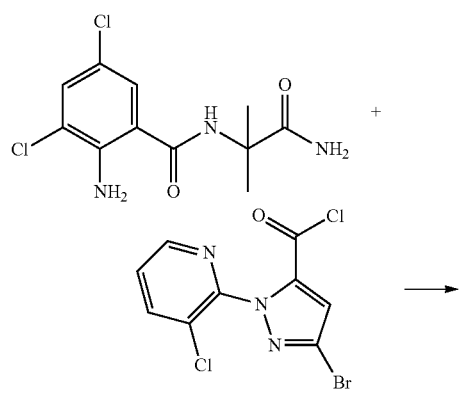

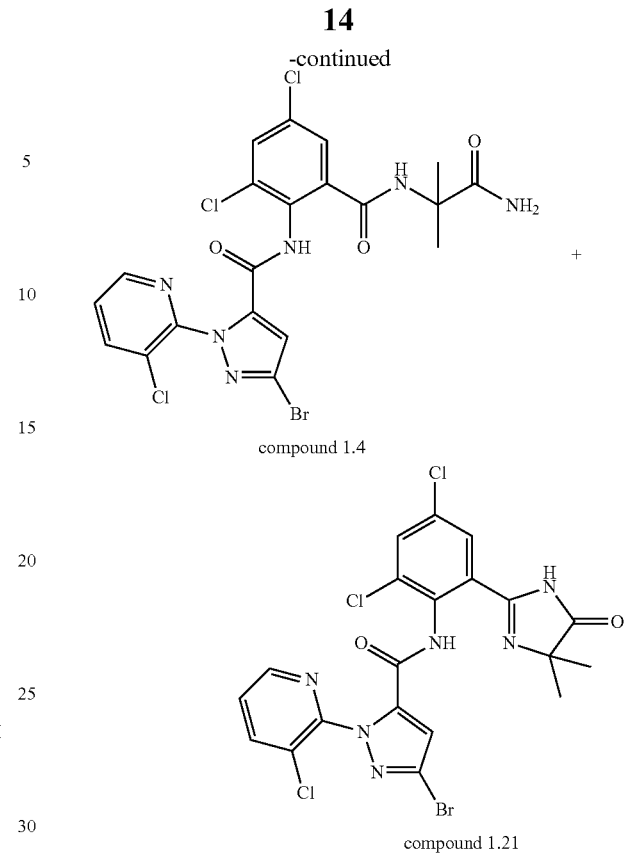

compound 1.4 compound 1.21

A slurry of 2-amino-3,5-dichloro-N-(2-cyanopropan-2-yl)benzamide (69 g, 254 mmol) and potassium hydroxide (15.65 g, 279 mmol) in alcohol (200 mL) at 0° C. was slowly added hydrogen peroxide (144 g, 1.27 mol, 30%). The mixture was stirred at room temperature for 24 hours and concentrated to give a red oil. The resultant was extracted with ethyl acetate (1000 mL) and water (500 mL). The organic layer was washed with saturated brine (500 mL), dried over anhydrous magnesium sulfate and concentrated by rotary evaporator. The residue was purified by silica gel column chromatography (Fluent:ethyl acetate:petroleum ether=1:1) to give the weak polar compound 2.10 (15.5 g) as a yellow solid in 22.2% yield. Melting point: 170-173° C.; And the strong polar compound 2.1 (32.2 g) as a white solid in 42.5% yield. Melting point: 166-168° C.

A solution of 2-amino-N-(1-amino-2-methyl-1-oxopropan-2-yl)-3,5-dichlorobenzamide (0.58 g, 2 mmol) in acetonitrile (10 mL) at room temperature was slowly added 3-bromo-1-(3-chloropyridin-2-yl)-1H-pyrazole-5-carbonyl chloride (0.77 g, 2.4 mmol, see WO03/015519) in acetonitrile (5 mL). The mixture was stirred at 60° C. for 2 hours and then concentrated. The resultant was added ethyl acetate (200 mL) and washed with saturated aqueous sodium hydrogen carbonate (50 mL) twice and saturated brine (50 mL) once, dried over anhydrous magnesium sulfate and concentrated by rotary evaporator. The residue was purified by silica gel column chromatography using 50% ethyl acetate/petroleum ether to give the weak polar (TLC: Rf is bigger) compound (0.07 g) as a white solid in 6.3% yield, which was compound 1.21 confirmed by $^1$H NMR, Melting point: 162-164° C.; And the strong polar (TLC: Rf is smaller) compound 1.4 (0.21 g) as a white solid in 18.3% yield, which was compound 1.4 confirmed by $^1$H NMR. Melting point: 164-168° C.

The compound 1.4 as main product can be prepared by the following processes:

A solution of 2-amino-N-(1-amino-2-methyl-1-oxopropan-2-yl)-3,5-dichlorobenzamide (10 g, 34.5 mmol) in acetonitrile (50 mL) at room temperature was slowly added 3-bromo-1-(3-chloropyridin-2-yl)-1H-pyrazole-5-carbonyl chloride (13.3 g, 41.4 mmol, see WO03/015519) in acetonitrile (20 mL). The mixture was stirred at room temperature for 12 hours and then concentrated. The resultant was added ethyl acetate (500 mL) and washed with saturated aqueous sodium hydrogen carbonate (100 mL) twice and saturated brine (100 mL) twice, dried over anhydrous magnesium sulfate and concentrated by rotary evaporator. The residue was purified by silica gel column chromatography (Fluent: ethyl acetate:petroleum ether=1:1) to give the compound 1.4 (9.2 g) as a white solid in 46.5% yield. Melting point: 164-168° C.

The compound 1.21 as main product can be prepared by the following processes:

A solution of 2-amino-N-(1-amino-2-methyl-1-oxopropan-2-yl)-3,5-dichlorobenzamide (10.7 g, 36.9 mmol) in toluene (100 mL) at room temperature was slowly added 3-bromo-1-(3-chloropyridin-2-yl)-1H-pyrazole-5-carbonyl chloride (14.2 g, 44.3 mmol, see WO03/015519) in toluene (20 mL). The mixture was heated to reflux for 1 hours and then concentrated. The resultant was added ethyl acetate (500 mL) and washed with saturated aqueous sodium hydrogen carbonate (100 mL) twice and saturated brine (100 mL) twice, dried over anhydrous magnesium sulfate and concentrated by rotary evaporator. The residue was purified by silica gel column chromatography (Fluent:ethyl acetate:petroleum ether=1:5) to give the compound 1.21 (7.7 g) as a white solid in 37.5% yield. Melting point: 162-164° C.

Example 2: Synthesis of Compound 1.3 and 1.20

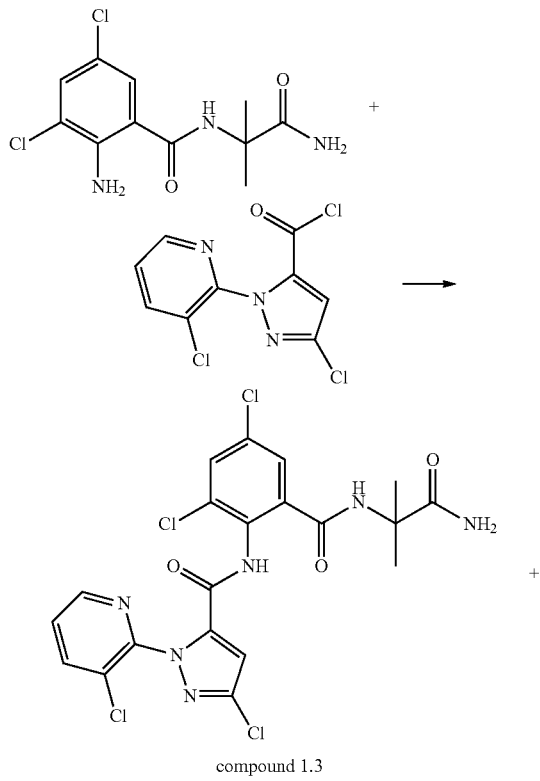

compound 1.3

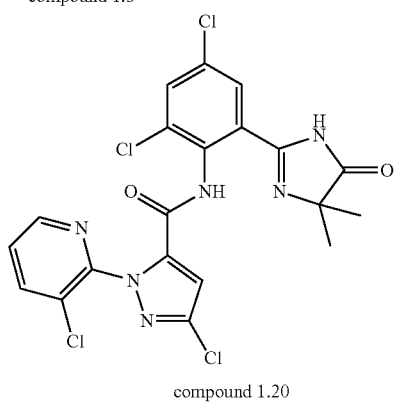

compound 1.20

A solution of 2-amino-N-(1-amino-2-methyl-1-oxopropan-2-yl)-3,5-dichlorobenzamide (0.5 g, 1.72 mmol) in acetonitrile (20 mL) at room temperature was slowly added 3-chloro-1-(3-chloropyridin-2-yl)-1H-pyrazole-5-carbonyl chloride (0.57 g, 2.06 mmol, see WO03/015519) in acetonitrile (10 mL). The mixture was heated to reflux for 1 hour and then concentrated. The resultant was added ethyl acetate (150 mL) and washed with saturated aqueous sodium hydrogen carbonate (50 mL) twice and saturated brine (50 mL) once, dried over anhydrous magnesium sulfate and concentrated by rotary evaporator. The residue was purified by silica gel column chromatography (Fluent:ethyl acetate:petroleum ether=1:1) to give the weak polar (TLC: Rf is bigger) compound (0.15 g) as a white solid in 17% yield, which was compound 1.20 confirmed by $^1$H NMR. Melting point: 152-157° C.; And the strong polar (TLC: Rf is smaller) compound (0.22 g) as a white solid in 20.7% yield, which was compound 1.3 confirmed by $^1$H NMR. Melting point: 158-162° C.

The compound 1.3 as main product can be prepared by the following processes:

A solution of 2-amino-N-(1-amino-2-methyl-1-oxopropan-2-yl)-3,5-dichlorobenzamide (40 g, 138 mmol) in acetonitrile (500 mL) at room temperature was slowly added 3-chloro-1-(3-chloropyridin-2-yl)-1H-pyrazole-5-carbonyl chloride (45.8 g, 165.6 mmol, see WO03/015519) in acetonitrile (100 mL). The mixture was stirred at room temperature for 12 hours and then concentrated. The resultant was added ethyl acetate (1000 mL) and washed with saturated aqueous sodium hydrogen carbonate (500 mL) twice and saturated brine (100 mL) twice, dried over anhydrous magnesium sulfate and concentrated by rotary evaporator. The residue was purified by silica gel column chromatography (Fluent:ethyl acetate:petroleum ether=1:1) to give the compound 1.3 (49 g) as a white solid in 64.8% yield. Melting point: 158-162° C.

The compound 1.20 as main product can be prepared by the following processes:

A solution of 2-amino-N-(1-amino-2-methyl-1-oxopropan-2-yl)-3,5-dichlorobenzamide (0.5 g, 1.72 mmol) in toluene (20 mL) at room temperature was slowly added 3-chloro-1-(3-chloropyridin-2-yl)-1H-pyrazole-5-carbonyl chloride (0.57 g, 2.1 mmol, see WO03/015519) in toluene (5 mL). The mixture was heated to reflux for 1 hours and then concentrated. The resultant was added ethyl acetate (100 mL) and washed with saturated aqueous sodium hydrogen carbonate (50 mL) twice and saturated brine (50 mL) twice, dried over anhydrous magnesium sulfate and concentrated by rotary evaporator. The residue was purified by silica gel column chromatography (Fluent:ethyl acetate:petroleum ether=1:5) to give the compound 1.20 (0.34 g) as a white solid in 38% yield. Melting point: 152-157° C.

Example 3: Synthesis of Compound 1.10 and 1.27

(1) Synthesis of 2-amino-3,5-dibromo-N-(2-cyanopropan-2-yl)benzamide

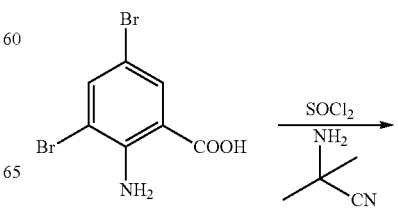

17

-continued

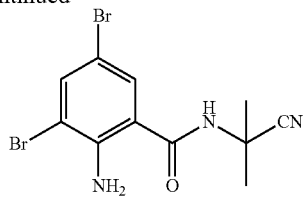

A solution of 2-amino-3,5-dibromobenzoic acid (23.5 g, 80 mmol) and sulfurous dichloride (28.4 g, 239 mmol) was heated to reflux for 6 hours. The reaction mixture was evaporated to dryness at reduced pressure to give a red oil.

A solution of 2-amino-2-methylpropanenitrile (6.7 g, 80 mmol) and triethylamine (12.1 g, 120 mmol) in tetrahydrofuran (200 mL) at room temperature was slowly added the red oil above in tetrahydrofuran (50 mL). The mixture was stirred for 12 hours at room temperature and then concentrated to dryness under vacuum. The resulting residue was extracted with ethyl acetate (300 mL) and water (100 mL). The organic layer was washed with saturated brine (50 mL), dried over anhydrous magnesium sulfate and concentrated to give a solid, which was purified by silica gel column chromatography (Fluent:ethyl acetate:petroleum ether=1:5) ether to give a yellow solid (19.47 g) in 63.6% yield.

(2) Synthesis of Compound 2.4 and Compound 2.12

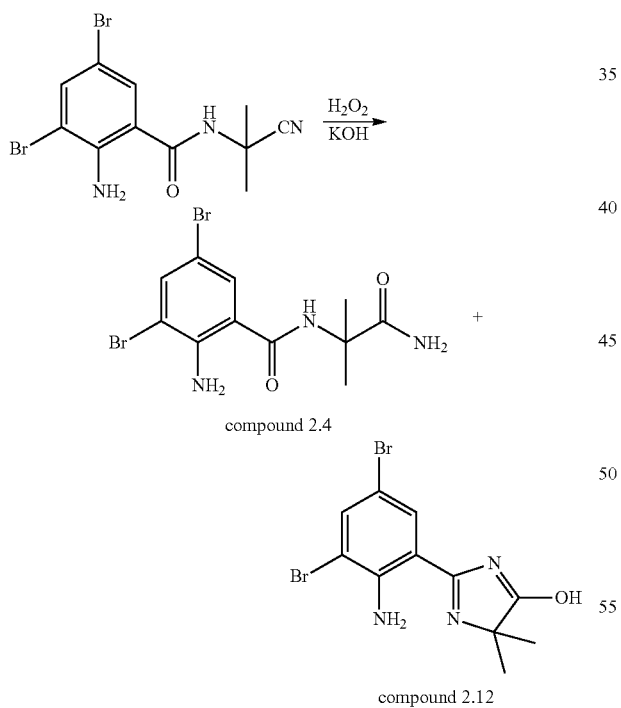

compound 2.4 compound 2.12

A slurry of 2-amino-3,5-dibromo-N-(2-cyanopropan-2-yl)benzamide (4 g, 11.1 mmol) and potassium hydroxide (0.93 g, 16.6 mmol) in alcohol (20 mL) was slowly added hydrogen peroxide (6.28 g, 55.4 mmol, 30%) at 0° C. and stirred for 1 hour. The mixture was stirred at room temperature for 12 hours and then concentrated. The resultant was extracted with ethyl acetate (100 mL) and water (50 mL).

18

The organic layer was washed with saturated brine, dried over anhydrous magnesium sulfate and concentrated by rotary evaporator. The ratio of the weak polar product (HPLC:the longer retention time) and the strong polar product (HPLC:the shorter retention time) is 32:68, and the total content is 90%. The resultant was purified by silica gel column chromatography (Fluent:ethyl acetate:petroleum ether=1:2) to give the weak polar compound 2.12 (0.83 g) as a white solid in 14.1% yield. Melting point: 180-183° C.; And the strong polar compound 2.4 (3.52 g) as a white solid in 77% yield. Melting point: 178-182° C.

(3) Synthesis of Compound 1.10 and Compound 1.27

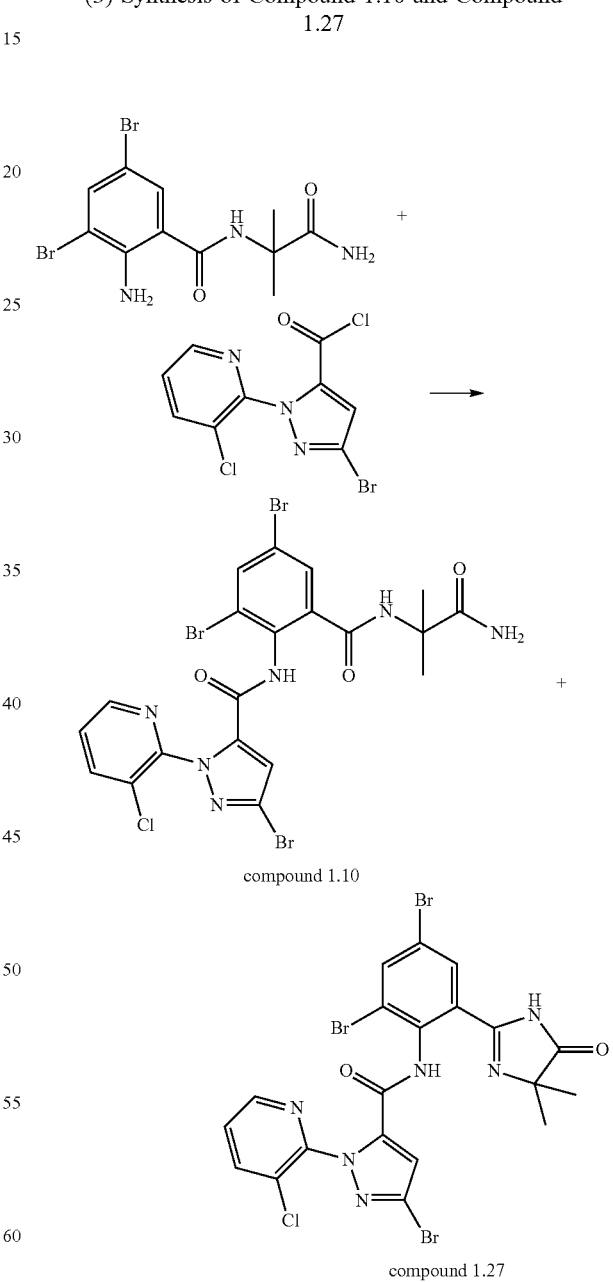

compound 1.10 compound 1.27

A solution of 2-amino-N-(1-amino-2-methyl-1-oxopropan-2-yl)-3,5-dibromobenzamide (1 g, 2.48 mmol) in acetonitrile (20 mL) at room temperature was slowly added 3-bromo-1-(3-chloropyridin-2-yl)-1H-pyrazole-5-carbonyl chloride (0.96 g, 2.98 mmol, see WO03/015519) in acetonitrile (10 mL). The mixture was heated to reflux for 2 hours and then concentrated. The resultant was added ethyl acetate (150 mL) and washed with saturated aqueous sodium hydrogen carbonate (50 mL) twice and saturated brine (50 mL) once, dried over anhydrous magnesium sulfate and concentrated by rotary evaporator to give a red oil (1.6 g) in 66% yield. The ratio of the weak polar product (HPLC:the longer retention time) and the strong polar product (HPLC:the shorter retention time) is 48:52, and the total content is 68%. The resultant was purified by silica gel column chromatography (Fluent:ethyl acetate:petroleum ether=1:1) to give the weak polar compound 1.27 (0.4 g) as a yellow solid in 22.5% yield. Melting point: 164-168° C.; And the strong polar compound 1.10 (0.52 g) as a white solid in 26.5% yield. Melting point: 172-175° C.

Example 4: Synthesis of Compound 1.38

(1) Synthesis of Compound 2.12

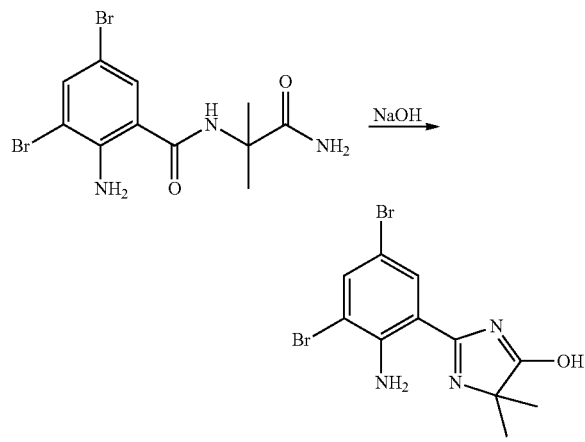

A solution of 2-amino-N-(1-amino-2-methyl-1-oxopropan-2-yl)-3,5-dibromobenzamide (1 g, 2.64 mmol) in dioxane (20 mL) at room temperature was slowly added 10% aqueous solution of sodium hydroxide (0.21 g, 5.28 mmol). The mixture was stirred at 80° C. for 4 hours and then concentrated. The resultant was extracted with ethyl acetate (100 mL) and water (50 mL). The organic layer was washed with saturated brine (50 mL), dried over anhydrous magnesium sulfate and concentrated by rotary evaporator. The residue was purified by silica gel column chromatography (Fluent:ethyl acetate:petroleum ether=1:3) to give compound 2.12 (0.73 g) as a white solid in 72% yield. Melting point: 178-182° C.

(2) Synthesis of Compound 1.38

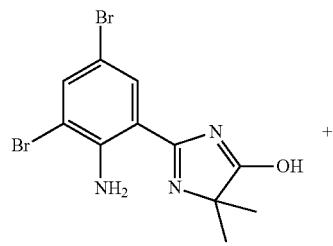

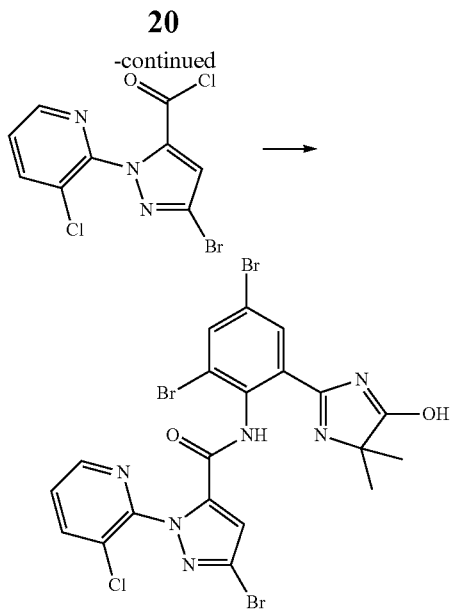

A solution of 2-(2-amino-3,5-dibromophenyl)-5,5-dimethyl-5H-imidazol-4-ol (0.7 g, 1.94 mmol) in acetonitrile (20 mL) at room temperature was slowly added 3-bromo-1-(3-chloropyridin-2-yl)-1H-pyrazole-5-carbonyl chloride (0.75 g, 2.33 mmol, see WO03/015519). The mixture was heated to reflux for 2 hours and then concentrated. The resultant was extracted with ethyl acetate (300 mL) and water (100 mL). The organic layer was washed with saturated brine (50 mL), dried over anhydrous magnesium sulfate and concentrated by rotary evaporator. The residue was purified by silica gel column chromatography (Fluent: ethyl acetate:petroleum ether=1:4) to give compound 1.38 (0.52 g) as a white solid in 41.5% yield. Melting point: 182-184° C.

The compounds of the general formula I can be prepared according to the above methods.

Example 5: Synthesis of $KC_1$ (1) Synthesis of 2-amino-3,5-dibromobenzoic acid

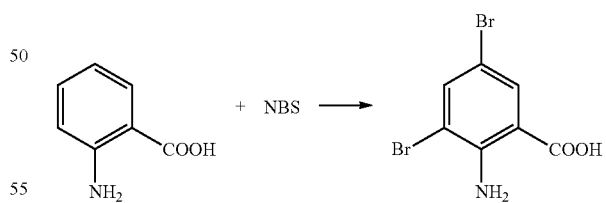

A solution of 2-aminobenzoic acid (10 g, 72.9 mmol) and N,N-dimethylformamide (50 mL) was stirred in a flask with three necks at room temperature till the 2-aminobenzoic acid was completely dissolved, 1-bromopyrrolidine-2,5-dione (27.3 g, 153 mmol) was added. The reaction mixture was stirred for 1 hour at 80° C. The mixture was poured into ice water with stirring vigorously. The solid that precipitated was collected by filtration, rinsed with water 2 times and air dried to give the product (17.8 g) as a yellow solid in 83% yield.

(2) Synthesis of methyl 2-(2-amino-3,5-dibromobenzamido)propanoate

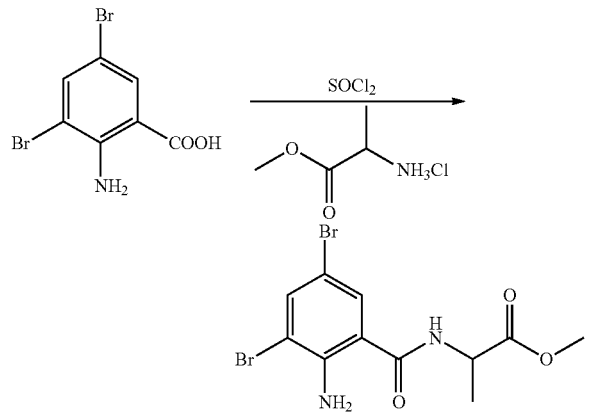

A solution of 2-amino-3,5-dibromobenzoic acid (17.75 g, 60 mmol) and sulfurous dichloride (21.48 g, 181 mmol) was heated to reflux for 3 hours. The reaction mixture was evaporated to dryness at reduced pressure to give a red oil.

A slurry of methyl D, L-alanine methyl ester hydrochloride (8.4 g, 60 mmol) and triethylamine (13.4 g, 132 mmol) in tetrahydrofuran (100 mL) at room temperature was slowly added the red oil above in tetrahydrofuran (50 mL). The mixture was stirred for 12 hours at room temperature and then concentrated to dryness under vacuum. The resulting residue was extracted with ethyl acetate (200 mL) and water (100 mL). The organic layer was washed with saturated brine (50 mL), dried over anhydrous magnesium sulfate and concentrated. The residue was purified by silica gel column chromatography (Fluent:ethyl acetate:petroleum ether=1:5) to give the product (8.2 g) as a white solid in 35% yield. Melting point: 107-109° C.

$^1$H NMR (300 MHz, DMSO-$d_6$): 8.79 (d, 1H), 7.80 (d, 1H), 7.62 (d, 1H), 6.52 (s, 2H), 4.42 (m, 1H), 3.67 (s, 3H), 1.41 (d, 3H).

(3) Synthesis of 2-amino-N-(1-amino-1-oxopropan-2-yl)-3,5-dibromobenzamide

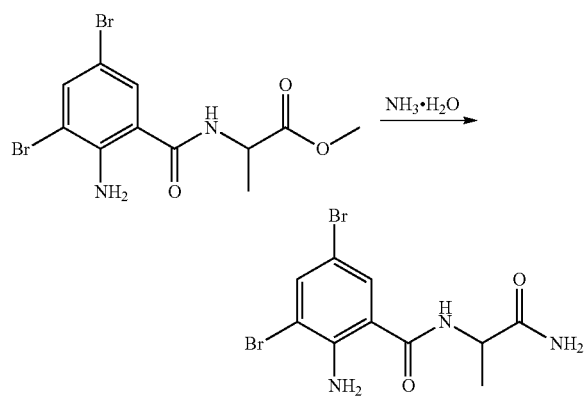

A solution of methyl 2-(2-amino-3,5-dibromobenzamido) propanoate (2 g, 5.26 mmol) in methanol (50 mL) at room temperature was slowly added 25% ammonia solution (37 g, 263 mmol). The mixture was heated to reflux for 8 hours and then concentrated to dryness under vacuum. The resulting residue was extracted with ethyl acetate (100 mL) and water (50 mL). The organic layer was washed with saturated brine (50 mL), dried over anhydrous magnesium sulfate and concentrated. The residue was purified by silica gel column chromatography (Fluent:ethyl acetate:petroleum ether=1:1) to give the product (0.74 g) as a white solid in 38.5% yield. Melting point: 210-213° C.

$^1$H NMR (300 MHz, DMSO-$d_6$): 8.45 (d, 1H), 7.80 (d, 1H), 7.56 (d, 1H), 7.27 (s, 1H), 6.83 (s, 1H), 6.45 (s, 2H), 4.36 (m, 1H), 1.34 (d, 3H).

In above procedure of 2-amino-N-(1-amino-1-oxopropan-2-yl)-3,5-dibromobenzamide, no obvious by-product was found in the reaction system by TLC and HPLC, and the cyclization product was not detected by $^1$H NMR in the crude product.

According to example 4 step 1, using 2-amino-N-(1-amino-1-oxopropan-2-yl)-3,5-dibromobenzamide as raw materiel, under the condition of sodium hydroxidethe, no obvious new product was found in the reaction system by TLC and HPLC, the crude product was confirm as raw materials via $^1$H NMR and the cyclization product was not detected in the crude product.

(4) Synthesis of $KC_1$

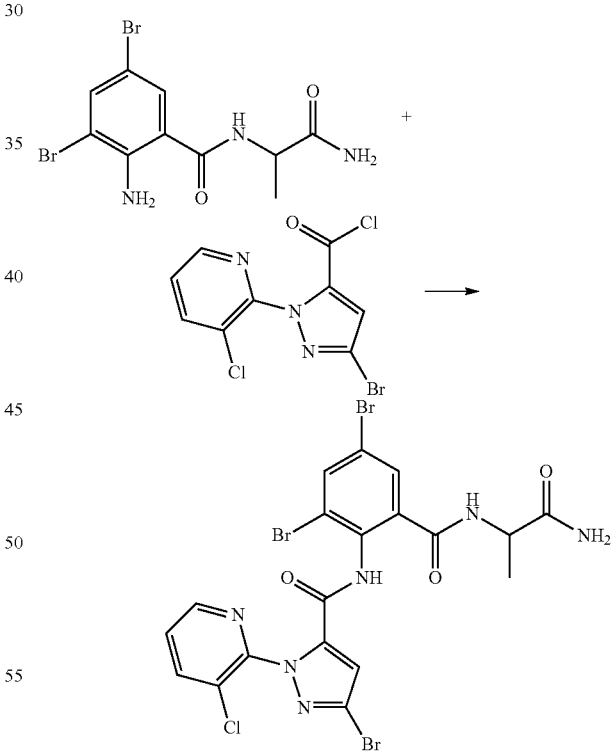

A solution of 2-amino-N-(1-amino-1-oxopropan-2-yl)-3,5-dibromobenzamide (0.5 g, 1.37 mmol) in acetonitrile (10 mL) at room temperature was slowly added 3-bromo-1-(3-chloropyridin-2-yl)-1H-pyrazole-5-carbonyl chloride (0.66 g, 2.05 mmol, see WO03/015519) in acetonitrile (5 mL). The mixture was heated to reflux for 2 hours. The reaction mixture was cooled down to room temperature and white solid was precipitated. The solid was isolated via filtration, washed with methanol (10 mL) and dried to give $KC_1$ (0.57 g) as a white solid in 64% yield. Melting point: 250-251° C.

$^1$H NMR (300 MHz, DMSO-$d_6$): 10.46 (s, 1H), 8.45 (s, 1H), 8.33 (d, 1H), 8.03 (d, 1H), 7.91 (s, 1H), 7.76 (s, 1H), 7.54 (t, 1H), 7.40 (s, 1H), 7.13 (s, 1H), 6.81 (s, 1H), 4.21 (m, 1H), 1.18 (d, 3H).

According to the above procedure of $KC_1$ no obvious by-product was found in the reaction system by TLC and HPLC, and the cyclization product was not detected by $^1$H NMR in the crude product.

According to the procedure of $KC_1$ above, $KC_2$ was produced as a white solid in 29.7% yield. Melting point: 243-244° C.

$^1$H NMR (300 MHz, DMSO-$d_6$): 10.39 (s, 1H), 8.45 (d, 1H), 8.29 (d, 1H), 8.07 (d, 1H), 7.56 (m, 2H), 7.44 (dd, 1H), 7.40 (s, 1H), 7.21 (s, 1H), 6.92 (s, 1H), 4.21 (m, 1H), 1.18 (d, 3H).

The physical properties of $KC_1$, $KC_2$ are consistent with the literature data (compound 47, 48 in CN1653051A).

Biological Test Examples

Example 6: Insecticidal Activity Tests

Exp. 6.1 Test Against Diamondback Moth

The test method is spraying. The leaves of cabbage grown in greenhouse were chosen, removed the surface waxy layer and perforated to get 3 cm diameter leaf discs by the hole puncher. The test compounds were sprayed on both sides of the discs by Airbrush according to the designed concentration from low to high dose. The cabbage discs were placed in 6 cm diameter Petri dish with filter paper. Tentest insects (3 instar) were introduced on each treatment after drying. Each treatment set the pure water as CK. The treated discs were placed in a certain condition. After 72 h, the number of surviving insects was investigated and the mortality rates were calculated.

Among some of the testing compounds, the following compounds exhibit mortality 80% or more against diamondback moth at 100 ppm: 1.3, 1.4, 1.5, 1.6, 1.7, 1.8, 1.9, 1.10, 1.13, 1.20, 1.21, 1.22, 1.23, 1.24, 1.25, 1.26, 1.27, 1.28, 1.35, 1.36, 1.37, 1.38, 1.39.

Among some of the testing compounds, the following compounds exhibit mortality 80% or more against diamondback moth at 10 ppm: 1.3, 1.4, 1.5, 1.6, 1.7, 1.8, 1.9, 1.10, 1.13, 1.20, 1.21, 1.22, 1.23, 1.24, 1.25, 1.26, 1.27, 1.28, 1.35, 1.36, 1.37, 1.38, 1.39.

According to above method, compound 1.3, 1.4, 1.8, 1.10 and $KC_1$, $KC_2$ (compound 47 and 48 in the patent CN1653051A) were chosen to parallel activity test against diamondback moth. The result was listed in Table 3.

TABLE 3

Parallel test result of compounds 1.3, 1.4, 1.8, 1.10 and $KC_1$, $KC_2$ against diamondback moth (mortality, %)

| Compounds | Concentration (ppm) | | |
|---|---|---|---|
| | 0.63 | 0.313 | 0.156 |
| | Mortality (%) | | |
| 1.3 | 100 | 100 | 87.5 |
| 1.4 | 100 | 100 | 100 |
| 1.8 | 100 | 75 | 52.1 |
| 1.10 | 100 | 81.3 | 62.5 |

TABLE 3-continued

Parallel test result of compounds 1.3, 1.4, 1.8, 1.10 and $KC_1$, $KC_2$ against diamondback moth (mortality, %)

| Compounds | Concentration (ppm) | | |
|---|---|---|---|
| | 0.63 | 0.313 | 0.156 |
| | Mortality (%) | | |
| $KC_1$ | 33.3 | 20 | 0 |
| $KC_2$ | 63.2 | 45.8 | 30 |

Exp. 6.2 Test Against Army Worm

The test method is spraying. The middle part of fresh corn leaves were chosen and cut into 3 cm sects. The test compounds were sprayed on both sides of the sects by Airbrush according to the designed concentration from low to high dose. The sects were placed in 6 cm diameter Petri dish with filter paper. Ten test insects (3 instar) were introduced on each treatment after drying. Each treatment set the pure water as CK. The treated sects were placed in a certain condition. After 72 h, the number of surviving insects was investigated and the mortality rates were calculated.

Among some of the testing compounds, the following compounds exhibit mortality 80% or more against army worm at 100 ppm: 1.3, 1.4, 1.5, 1.6, 1.7, 1.8, 1.9, 1.10, 1.13, 1.20, 1.21, 1.22, 1.23, 1.24, 1.25, 1.26, 1.27, 1.28, 1.35, 1.36, 1.37, 1.38, 1.39, 1.40.

Among some of the testing compounds, the following compounds exhibit mortality 80% or more against army worm at 10 ppm: 1.3, 1.4, 1.6, 1.8, 1.13, 1.20, 1.21, 1.22, 1.23, 1.24, 1.25, 1.26, 1.27, 1.28, 1.35, 1.36, 1.37, 1.38, 1.39, 1.40.

According to above method, compound 1.3, 1.4, 1.8, 1.10 and $KC_1$, $KC_2$ (compound 47 and 48 in the patent CN1653051A) were chosen to parallel activity test against army worm. The result was listed in Table 4.

TABLE 4

Parallel test result of compounds 1.3, 1.4, 1.8, 1.10 and $KC_1$, $KC_2$ against army worm (mortality, %)

| Compounds | Concentration (ppm) | | |
|---|---|---|---|
| | 10 | 5 | 2.5 |
| | Mortality (%) | | |
| 1.3 | 100.0 | 81.2 | 64.3 |
| 1.4 | 92.8 | 86.6 | 50.0 |
| 1.8 | 100 | 50.0 | 43.7 |
| 1.10 | 100 | 87.5 | 62.5 |
| $KC_1$ | 18.0 | 0.0 | 0.0 |
| $KC_2$ | 61.6 | 16.7 | 0.0 |

Exp. 6.3 Test Against Green Peach Aphid

According to the solubility of test compounds, the compounds are dissolved in acetone or dimethyl sulfoxide, and then diluted with 0.1% aqueous solution of Tween 80 to form the test liquid 50 ml, the content of acetone or dimethyl sulfoxide in the total solution is not more than 10%.

The 6 cm diameter Petri dish with a layer of filter paper was chosen, a moderate amount of water was added to preserve moisture. A suitable piece of cabbage leaf with 30-50 green peach aphids was excised from a culture plant. Remove the winged and positive aphids, the leaf was placed to the Petri dish above with back upward. The test compounds were sprayed on both sides of the leaf by Airbrush (spray pressure: 10 psi, equate to 0.7 kg/cm$^2$; spray volume: 0.5 mL; spray distance: 15-20 cm). The treated Petri dishes were placed in a chamber of 23-25° C., 40%-60% relative humidity, L/D 13 h: 11 h. To keep the leaf fresh, a moderate amount of water was added to the Petri dish during the observation. After 48 h, the number of surviving insects was investigated and the mortality rates were calculated.

Among some of the testing compounds, the following compounds exhibit mortality 80% or more against green peach aphid at 600 ppm: 1.3, 1.4, 1.5, 1.6, 1.8, 1.9, 1.10, 1.13, 1.20, 1.21, 1.22, 1.23, 1.26, 1.27, 1.36, 1.37, 1.38, 1.39.

Among some of the testing compounds, the following compounds exhibit mortality 80% or more against green peach aphid at 100 ppm: 1.3, 1.4, 1.5, 1.6, 1.7, 1.8, 1.9, 1.10, 1.13, 1.20, 1.22, 1.23, 1.26, 1.27, 1.36, 1.37.

According to above method, compound 1.3, 1.4, 1.8, 1.10 and KC$_1$, KC$_2$ (compound 47 and 48 in the patent CN1653051A) were chosen to parallel activity test against green peach aphid. The result was listed in Table 5.

TABLE 5

Parallel test result of compounds 1.3, 1.4, 1.8, 1.10 and KC$_1$, KC$_2$ against green peach aphid (mortality, %)

| Compounds | Concentration (ppm) | | |
|---|---|---|---|
| | 10 | 5 | 2.5 |
| | Mortality (%) | | |
| 1.3 | 100.0 | 100.0 | 100.0 |
| 1.4 | 100.0 | 100.0 | 90.1 |
| 1.8 | 100.0 | 100.0 | 89.3 |
| 1.10 | 100.0 | 100.0 | 100.0 |
| KC$_1$ | 15.1 | 0.0 | 0.0 |
| KC$_2$ | 70.4 | 57.6 | 0.0 |

Exp. 6.4 Test of Absorption Activity

The 3 cm horsebean seedling that pre-infested by a certain number of black bean aphids (2 days instar) was chosen and transplanted to a paper cup loaded with fine sand. According to the test, the test compounds were treated to a solution and poured into the cup. After 48 h, the number of surviving insects was investigated and the mortality rates were calculated.

TABLE 6

The absorption activity parallel test result of compounds 1.3, 1.4 and cyantraniliprole against black bean aphid (mortality, %)

| Compound | Mortality, % | | |
|---|---|---|---|
| | 10 mg/L | 2.5 mg/L | 0.625 mg/L |
| 1.3 | 100 | 100 | 100 |
| 1.4 | 100 | 100 | 100 |
| Cyantraniliprole | 100 | 54.6 | 30.0 |

Exp. 6.5 Field Test Against Apple Tree Aphids

The test was carried out in the institute of pomology of CAAS orchard in June 2014, using starkrimson as the test sample, the apple tree aphids were in preliminary stage. The test method is spraying using the stretcher power sprayer (ZL-22-160), each treatment repeated 4 times. The number of initial aphids was investigated before spraying. After 2 days, 7 days, 14 days, the number of surviving aphids was investigated respectively and the control efficiency were calculated. 10% Cyantraniliprole SC was commercial available which was bought from DuPont Agricultural Chemicals Ltd., Shanghai.

TABLE 7

The results of the field test against apple tree aphids

| Compound | Dose | Mortality (%) | | |
|---|---|---|---|---|
| | | 2 day | 7 day | 14 day |
| 1.3 | 25 mg/L | 78.92 abc | 93.46 a | 93.08 a |
| | 50 mg/L | 83.49 abc | 96.11 a | 96.72 a |
| 10% Cyantraniliprole SC | 50 mg/L | 60.68 c | 75.29 b | 54.38 c |

Exp. 6.6 Field Test Against Cabbage Aphids

The test was carried out in the institute of Vegetables and Flowers Chinese Academy of Agriculture Sciences Nankou base, using cabbages (JINGFENG) as the test plant. The test compounds dosage were 15 g a.i./hm$^2$ and 10% Cyantraniliprole SC dosage was 30 g a.i./hm$^2$ which were sprayed evenly to the whole plant using backpack manual sprayer ("MATABI" SUPER GREEN 16) at the spray volume of 750 L/hm$^2$. Each treatment repeated 4 times, arranged with randomized blocks. 5 spots were chosen from each area using diagonal method, each spot contains 2 cabbages, the 10 cabbages above were investigated in the area. The number of initial cabbage aphids was investigated before spraying. After 1 day, 3 days, 7 days, 14 days, the number of surviving aphids was investigated respectively and the control efficiency were calculated.

decline ratio of insect (%)=(insect number before pesticide application−insect number after pesticide application)/(insect number before pesticide application)×100% control efficiency (%)=(treatment area decline ratio of insect−CK area decline ratio of insect)/(100−CK area decline ratio of insect)×100%  Calculation Method:

10% Cyantraniliprole SC was bought from DuPont Agricultural Chemicals Ltd., Shanghai. The result was shown in table 8.

TABLE 8

The results of the field test against cabbage aphids

| Compound | Dose (g a.i./hm$^2$) | Mortality (%) | | | |
|---|---|---|---|---|---|
| | | 1 d | 3 d | 7 d | 14 d |
| 1.3 | 15 | 80.78 c | 87.22 b | 92.57 ab | 91.77 ab |
| 1.4 | 15 | 84.40 abc | 91.03 ab | 95.58 ab | 91.79 ab |
| 10% Cyantraniliprole SC | 30 | 88.78 abc | 92.25 ab | 84.83 b | 84.12 b |

The invention claimed is:

1. A pyrazolyl amide compound represented by the general formula I:

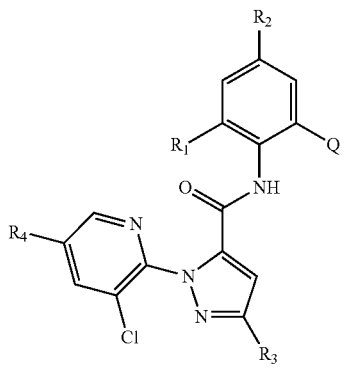

wherein:
R₁ is Cl or Br;
R₂ is Cl or Br;
R₃ is Cl or Br;
R₄ is H;

Q is Q₁ shown as follows:

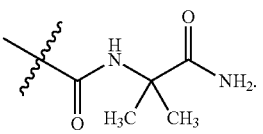

2. The compound according to claim 1, characterized in that wherein:
R₁ is Cl;
R₂ is Cl;
R₃ is Cl or Br;
R₄ is H;
Q is Q₁.

3. An insecticidal composition, characterized in that wherein: comprising the characterized compounds of general formula I of claim 1 and an acceptable carrier in agriculture, forestry or public health, in which the weight percentage of active ingredient(s) is 1%-99%.

4. A method for controlling insects, characterized in that wherein: applying the composition of claim 3 to pests or its growth medium with effective dosage within a range of from 10 g/ha to 1000 g/ha.

* * * * *